United States Patent [19]

Lutz et al.

[11] 4,021,483

[45] May 3, 1977

[54] 2-CHLORO-N-ISOPROPYL-2',3'-DIMETHYLACETANILIDE AS A HERBICIDAL AGENT

[75] Inventors: Albert William Lutz, Princeton; Robert Eugene Diehl, Trenton, both of N.J.

[73] Assignee: American Cyanamid Company, Stamford, Conn.

[22] Filed: July 25, 1975

[21] Appl. No.: 599,235

[52] U.S. Cl. .............................. 260/562 B; 71/118
[51] Int. Cl.² ..................................... C07C 103/375
[58] Field of Search ................................ 260/562 B

[56] References Cited

UNITED STATES PATENTS

| | | | |
|---|---|---|---|
| 2,863,752 | 12/1958 | Hamm et al. | 260/562 B |
| 3,268,584 | 8/1966 | Olin | 260/562 B |
| 3,475,157 | 10/1969 | Olin | 260/562 B |
| 3,541,153 | 11/1970 | Sandridge | 260/577 |
| 3,867,446 | 2/1975 | Matolcsy et al. | 260/562 B |

FOREIGN PATENTS OR APPLICATIONS

| | | | |
|---|---|---|---|
| 1,337,529 | 8/1963 | France | 260/562 B |
| 2,027,822 | 12/1970 | Germany | |

*Primary Examiner*—Arthur P. Demers
*Attorney, Agent, or Firm*—Harry H. Kline

[57] ABSTRACT

This invention relates to 2-chloro-N-isopropyl 2',3'-dimethylacetanilide, a method for the preparation thereof, and a method for the control of undesirable plant species therewith.

1 Claim, No Drawings

2-CHLORO-N-ISOPROPYL-2',3'-DIMETHYLACETANILIDE AS A HERBICIDAL AGENT

BACKGROUND OF THE INVENTION

Chloroacylanilides and a method for the preparation thereof from anilines and chlorocarboxylic acids are disclosed in the German Offenlegungsschift No. 2,027,822, filed on June 7, 1969. This disclosure generically defines a class of compounds which encompasses the compound of the subject invention and describes certain analogues and homologues thereof. However, this publication does not specifically identify the compound of the instant invention and fails completely to recognize its unique character. Surprisingly, it has been found that 2-chloro-N-isopropyl-2',3'-dimethylacetanilide is markedly superior to its closest homologs for the control of undesirable plant species. Moreover, it has been found that said acetanilide compound can be prepared from 3-nitro-o-xylene, an undesirable by-product formed in the manufacture of a recently developed, highly effective, substituted dinitroaniline herbicidal agent. To the present, it has been considered necessary to burn this undesirable byproduct in order to prevent its release into the atmosphere in the vicinity of the manufacturing facility for said herbicidal agent. However, even this measure of ignition of the 3-nitro-o-xylene is less desirable than the conversion of said by-product to a useful herbicide. Obviously, ignition of 3-nitro-o-xylene represents an economic loss in the process of manufacture of the substituted dinitroaniline herbicide and results in the release of oxides of carbon and nitrogen into the atmosphere. With the present invention, it is thus possible to prevent environmental contamination and to provide a highly effective weed control agent utilizing an economically advantageous process, thereby fulfilling a long felt need in the art.

In addition to the German application above-identified, it is further noted that South African Pat. No. 62/3650, dated Aug. 28, 1062, describes alpha-haloacetamides generically as herbicidal agents. As in the German disclosure, the South African patentee does not disclose 2-chloro-N-isopropyl-2',3'-dimethylacetanilide specifically and fails to recognize its unique character.

SUMMARY OF THE INVENTION

This invention relates to the compound, 2-chloro-N-isopropyl-2',3'-dimethylacetanilide, to a process for its preparation, and to a method for the control of undesirable plant species therewith.

In accordance with the present invention, 2-chloro-N-isopropyl 2',3'-dimethylacetanilide can be prepared by the reductive alkylation of 3-nitro-o-xylene with acetone to form N-isopropyl-2,3-xylidine, followed by chloroacetylation thereof, with chloroacetyl chloride or chloroacetic anhydride, to yield the above-said dimethylacetanilide.

This process can be graphically illustrated as follows:

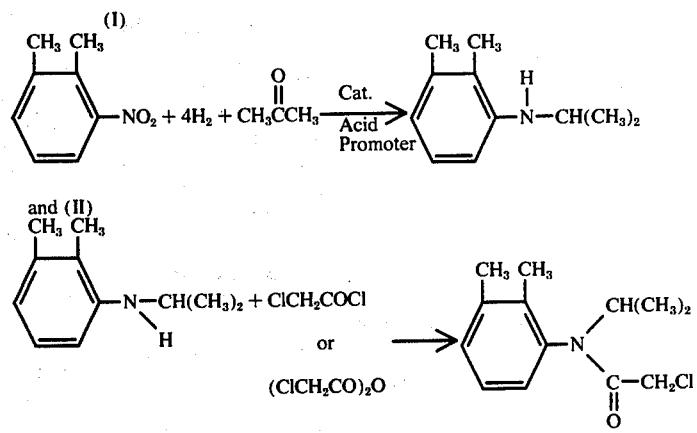

In practice the reductive alkylation of 3-nitro-o-xylene is, preferably, conducted in the presence of a noble metal catalyst, such as platinum or palladium, hydrogen gas and an acid promoter havving a pKa value ranging between about 0.3 and 2.0 and, preferably, from 0.5 to 1.0.

The noble metal catalyst is preferably in finely divided form and, preferably, carried on a suitable support such as carbon, silica, alumina or the like.

The reductive alkylation is generally conducted in a pressure reactor under superatmospheric conditions and at an elevated temperature. Typically, the 3-nitro-o-xylene, acetone, novel metal catalyst and acid promoter are charged to a reactor. The reactor is then preferably deoxygenated by evacuation, followed by purging with nitrogen. The reactor is then pressurized to about 10 to 120 psig and, preferably, 40 to 80 psig, with hydrogen gas and the reaction mixture is heated to between about 40° C and 150° C and preferably 60° C to 100° C. The reaction is generally completed in from 10 minutes to several hours, and when complete, the mixture is cooled and the pressure in the reactor reduced, as by venting.

Satisfactory results may be achieved when the amount of acid used in the promoter system is as low as 0.1 mole per hundred moles of the 3-nitro-o-xylene. The upper limit of acid is only limited by practical considerations. The most preferable amount of acid used ranges from 1 to 3 moles of acid per hundred moles of the 3-nitro-o-xylene.

The noble metal catalyst is preferably used in an amount which is not less than about 0.3 g of noble metal (preferably platinum) per mole of the 3-nitro-o-xylene being alkylated. If the catalyst is adsorbed on a substrate, adjustments should be made in the amount of material used so that at least an amount of about 0.3 g of metal per mole of the o-xylene is present, notwithstanding the quantity of the substrate on which it is adsorbed.

The catalyst used in the process of this invention can be recycled in a conventional manner, but it is preferable to fortify the spent catalyst with sufficient fresh catalyst to maintain its level of activity. The amount of fresh catalyst added is normally less than 10% of the original usage and is, preferably, 2% to 5% of this usage.

The catalyst can be pre-reduced or one can utilize the noble metal oxide and reduce it to the metal in the reaction mixture.

While the actone and 3-nitro-o-xylene react on approximately an equimolar basis, it is usually preferable to employ a 1.1:1 to 2.2:1 ratio of acetone to the starting compound. It is likewise desirable to employ a mole ratio of promoter acid, preferably an aromatic sulfonic acid, to starting compound in the range of 0.02:1 to 0.03:1 and further a mole ratio of metal catalyst to starting compound in the range of 0.05:1 to 0.15:1. A large excess of hydrogen gas is, likewise, generally employed in the reaction.

Illustrative of the acids which may be employed as promoters for the reductive alkylation are β-naphthalene sulfonic acid, p-toluenesulfonic acid, 3,5-dihydroxybenzoic acid, ethylbenzenesulfonic acid, trichloroacetic acid, dichloroacetic acid and trifluoroacetic acid.

Chloroacetylation of N-isopropyl-2,3-xylidine, formed by the above-described reductive alkylation process, is achieved using a mole ratio of the chloroacetylating agent to N-isopropyl-2,3-xylidine of from about 0.5:1 to 2:1. The reaction is preferably conducted in the presence of an organic solvent at an elevated temperature, preferably between about 60° C and 150° C.

Exemplary of the organic solvents which may be utilized therein are benzene, toluene, xylene, hexane, diethylether and the like.

In practice, it may also be desirable to include an acid acceptor, such as alkali metal and alkaline earth metal carbonates, bicarbonates, hydroxides or the like in the reaction mixture to neutralize the acid formed by the reaction.

Suitable chloroacetylating agents are chloroacetyl chloride and chloroacetic anhydride.

Advantageously, 2-chloro-N-isopropyl-2',3'-dimethylacetanilide may also be prepared by the reductive alkylation of 2,3-xylidine under essentially the same conditions reported for the reductive alkylation of 3-nitro-o-xylene, excepting that the acetone to aniline ratio may range from 1.1:1 to 10:1, the mole percent of acid promoter may range from 0.1 to 10 mole percent based on the aniline and the mole percent of metal catalyst, preferably platinum, ranges from 0.005:1 to 0.25:1, based on said aniline.

As indicated, 2-chloro-N-isopropyl-2',3'-dimethylacetanilide is a highly effective preemergence herbicidal agent useful for the control of undesirable grasses. It may be applied as a preemergence herbicide to soil containing seeds of undesirable grass plants. The compound is preferably applied in the form of a dilute liquid spray; however, it may also be applied in the form of a finely divided solid, such as a dust or granular product.

For application as liquid sprays, said compounds are generally prepared as wettable powders or emulsifiable concentrates which are dispersed in water or other inexpensive liquid diluent and applied as dilute solutions or suspension to soil containing seeds of undesirable plants, particularly undesirable grasses.

Wettable powder formulations can be prepared by grinding together about 25% to 95%, by weight, of the active ingredient and a solid diluent, such as attapulgite, kaolin, or diatomaceous earth. The thus-prepared solid formulation is admixed with about 1% to 5%, by weight, of a dispersing agent, such as the calcium salt of a polymerized alkyl aryl sulfonic acid, sodium lignosulfonate, or the sodium salt of condensed naphthalene sulfonic acid, and blending therewith about 1% to 5% by weight of a surfactant, such as alkyl phenoxy polyoxyethylene ethanol, sodium alkyl naphthalene sulfonate, or a polyoxyethylated vegetable oil. The formulated powder is then generally dispersed in water or other suitable diluent at the site of application.

In practice it has been found that approximately 0.14 to 4.48 kg/ha and, preferably, 0.28 to 2.24 kg/ha of the compound 2-chloro-N-isopropyl-2',3'-dimethylacetanilide, will provide excellent control of undesirable grass plants, such as, crabgrass, barnyard grass, and foxtails.

Advantageously, it has also been observed that the above-identified compound is highly selective for grass plants and can be used effectively for the control thereof in the presence of crops such as corn, cotton and soybeans.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Reductive Alkylation of 3-nitro-o-xylene to form N-isopropyl-2,3-xylidine

A mixture of 30.2 g (0.20 mole) of 3-nitro-o-xylene, 23.2 g (0.40 mole) of acetone, 1.2 g. of 5% platinum on carbon, and 0.90 g (2 mole percent) of 2-naphthalene sulfonic acid is charged to an autoclave and the autoclave is sealed, evacuated, purged with nitrogen, and then pressurized with hydrogen gas to 47 psig. The temperature of the contents of the autoclave is raised to 60° C and held at 60° C to 65° C for about three-fourths of an hour and then lowered to about 25° C. The autoclave is vented, opened and the contents withdrawn and filtered to separate the catalyst. The lower layer of the filtrate is separated in a separatory funnel and the catalyst cake, filter flask and separatory funnel are rinsed with 10 ml of acetone which is combined with the organic phase and evaporated to constant weight. The resulting product is N-isopropyl-2,3-xylidine having a yield and purity above 95%.

The above procedure is repeated, excepting that p-toluenesulfonic acid is substituted for β-naphthalene sulfonic acid and palladium on silica catalyst is substituted for platinum on carbon catalyst, to yield desired compound.

EXAMPLE 2

The process of Example 1 is repeated in every detail except that there is substituted for the 3-nitro-o-xylene, 2,3-xylidine. A good yield of N-isopropyl-2,3-xylidine is then obtained.

EXAMPLE 3

Preparation of N-isopropyl-2,3-Xylidine by reductive alkylation of 2,3-dimethylaniline A mixture of 12 g of 2,3-xylidine, 60 ml of acetone and 30 g of type 5A sieves (alumino silicate) are placed in a flask and stirred overnight at room temperature. The mixture is filtered and the filtrate concentrated in vacuo to yield an oily residue. This residue is taken up in 100 ml of methanol, treated with 4.0 1 g of sodium borohydride and warmed to above 15° C. The mixture is made acidic, then basic, and finally extracted with ether to yield 11.4 g of N-isopropyl-2,3-xylidine which is verified by infra-red spectra and NMR.

EXAMPLE 4

Chloroacetylation of N-isopropyl-2,3-xylidine

A mixture of 8.0 g (0.066 mole) of N-isopropyl-2,3-xylidine, 4.0 g (0.035 mole) chloroacetyl chloride, and 200 ml of benzene are charged to a flask and refluxed for 2 hours. After refluxing the reaction mixture is cooled, stripped in vacuo and then taken up in ether. Pentane is then added to the mixture to precipitate the hydrochloride salt, which is removed by filtration.

The filtrate is then concentrated and the residue taken up in ether. The mixture is washed twice with dilute hydrochloric acid and then with water. The ether layer is separated and dried. Removal of the ether leaves an oil which, on standing, solidifies as a waxy solid. Recrystallization from pentane yields 4.7 g of product 2-chloro-N-isopropyl-2′,3′-dimethylacetanilide with 97% purity. Calculated for $C_{13}H_{18}ClNO$: C, 65.13; H, 7.52; N, 5.84. Found: C, 64.01; H, 7.36; N, 5.81.

Following the above procedure but substituting equimolar molar amounts of N-isopropyl-2,3-xylidine and chloroacetic anhydride for the N-isopropyl-2,3-xylidine and chloroacetyl chloride employed therein, there is obtained 2-chloro-N-isopropyl-2′,3′-dimethylacetanilide in substantially the same yield and purity.

EXAMPLE 5

Selective Preemergence herbicidal activity

The selective preemergence herbicidal activity of test compounds is evaluated by the following procedure. In these tests seeds of a variety of grass and crop plants are separately mixed with potting soil and the mixture placed on top of several inches of potting soil in separate cups. After planting, the cups are sprayed with the selected aqueous-acetone solution containing the test compound in sufficient quantity to provide the desired equivalent of 0.07 kg to 4.48 kg per hectare per cup.

The treated cups are then placed on greenhouse benches and cared for in the usual manner, in accordance with greenhouse procedures. Three weeks after treatment, the tests are terminated and each cup is examined and rated according to the defined Herbitoxicity Index given in each of the tables below.

Herbitoxicity Index

9 = 100% Reduction in stand
9 = 1 or 2 Stunted plants remaining
8 = 85– <100% Reduction in stand
7 = 70– <85% Reduction in stand
6 = 60– <70% Reduction in stand
5 = 50–<60% Reduction in stand
4 = 40–<50% Reduction in stand
3 = 30–<40% Reduction in stand
2 = 20–<30% Reduction in stand
1 = 10– <20% Reduction in stand Abbreviations for the plant species employed in the herbicidal evaluations hereinafter reported.

Ba = Barnyard grass — *Echinochloa crusgalli*
Cr = Crabgrass — *Digitaria sanguinalis*
FO = Greek Foxtail — *Setaria viridis*
TW = Tea Weed — *Sida spinosa*
Cor = Corn — *Zea mays*
Cot = Cotton — *Gossypium hirsutam*
Ri = Rice — *Oryza sativa*
SOY = Soybeans — *Glycine max*

From the data presented in Tables I and II below, it can be seen that in side by side tests 2-chloro-N-isopropyl-2′,3′-dimethylacetanilide is highly selective for the control of undesirable grass plants in the presence of crops such as corn, cotton and rice and approximately twice as effective for the control of said grass plants as the commercial herbicide propachlor, a relatively closely related compound thereto.

The 2-chloro-N-isopropyl-2′,3′-dimethylacetanilide is, likewise vastly superior to the other related compounds shown in Table II.

Table I

Selective Preemergence Herbicidal Activity

| Test Compounds | Rate kg/ha | Grasses | | | Crops | | |
|---|---|---|---|---|---|---|---|
| | | Ba | Cr | FO | Cor | Cot | Ri |
| 2-Chloro-N-isopropyl-2′,3′-dimethylacefanilide | 4.48 | 9 | 9 | 9 | 2 | 2 | 0 |
| | 1.12 | 9 | 9 | 9 | 0 | 0 | 0 |
| | 0.56 | 9 | 9 | 8 | 0 | 0 | 0 |
| | 0.28 | 8 | 8 | 8 | 0 | 0 | 0 |
| | 0.14 | 7 | 7 | 8 | 0 | 0 | 0 |
| Propchlor (Commercial) | 4.48 | 9 | 9 | 9 | 2 | 5 | 2 |
| | 1.12 | 8 | 8 | 9 | 0 | 0 | 0 |
| | 0.56 | 8 | 8 | 9 | 0 | 0 | 0 |
| | 0.28 | 9 | 7 | 7 | 0 | 0 | 0 |
| | 0.14 | 2 | .1 | 3 | 0 | 0 | 0 |

Table II

Selective Preemergence Herbicidal Activity

| Test Compounds | Rate kg/ha | Grasses | | | Crops | | | |
|---|---|---|---|---|---|---|---|---|
| | | Ba | Cr | FO | Cor | Cot | Ri | Soy |
| 2-Chloro-N-isopropyl-2′,3′-dimethylacetanilide | 1.12 | 9 | 9 | 9 | 0 | 0 | 0 | 7 |
| | 0.56 | 9 | 8 | 8 | — | — | — | 3 |
| | 0.28 | 8 | 7 | 8 | — | — | — | 0 |
| | 0.14 | 8 | 3 | 6 | — | — | — | — |
| | 0.07 | 6 | 1 | 3 | — | — | — | — |

Table II-continued

| Test Compounds | Rate kg/ha | Grasses | | | Crops | | | |
|---|---|---|---|---|---|---|---|---|
| | | Ba | Cr | FO | Cor | Cot | Ri | Soy |
| (structure with CH₃, CH₃, CH₂OCH₃, N, CO—CH₂Cl) | 1.12 | 9 | 3 | 9 | 0 | 0 | 0 | 2 |
| | 0.56 | 9 | 1 | 6 | — | — | — | 2 |
| | 0.28 | 6 | 0 | 1 | — | — | — | 0 |
| | 0.14 | 6 | 0 | 0 | — | — | — | — |
| | 0.07 | 1 | 0 | 0 | — | — | — | — |
| (structure with CH₃, CH₃, CH₂(C₂H₅)₂, N, CO—CH₂Cl) | 1.12 | 9 | 0 | 7 | 0 | 0 | 0 | 1 |
| | 0.56 | 8 | 0 | 5 | — | — | — | 0 |
| | 0.28 | 6 | 0 | 3 | — | — | — | — |
| | 0.14 | 0 | 0 | 0 | — | — | — | — |
| | 0.07 | 0 | 0 | 0 | — | — | — | — |

We claim:

1. The compound: 2-chloro-N-isopropyl-2',3'-dimethylacetanilide.

* * * * *